United States Patent
Martoral et al.

[11] Patent Number: 5,934,905
[45] Date of Patent: Aug. 10, 1999

[54] FLEXIBLE SCULPTING TOOL FOR DENTAL UNITS

[76] Inventors: Maximo Martoral, 3633 Marvin Ave., Cleveland, Ohio 44109; Guillermo Padin, 3102 Warren Rd., Cleveland, Ohio 44111

[21] Appl. No.: 09/042,766

[22] Filed: Mar. 17, 1998

Related U.S. Application Data

[60] Provisional application No. 60/043,363, Apr. 1, 1997.

[51] Int. Cl.⁶ .................................................. A61C 3/02
[52] U.S. Cl. ............................ 433/144; 30/342; 30/DIG. 6
[58] Field of Search ...................................... 433/141, 143, 433/144; 606/167, 172; 30/340, 342, DIG. 6

[56] References Cited

U.S. PATENT DOCUMENTS

| | | |
|---|---|---|
| 1,532,570 | 4/1925 | Basmaison . |
| 1,586,302 | 5/1926 | Funk ........................................ 433/141 |
| 1,800,254 | 4/1931 | Holmes . |
| 1,968,242 | 7/1934 | Birch . |
| 2,039,926 | 5/1936 | Paradise . |
| 2,298,975 | 10/1942 | Shelburne . |
| 2,468,946 | 5/1949 | Sherman . |
| 2,659,143 | 11/1953 | Baker . |
| 2,865,100 | 12/1958 | Gilbert . |
| 3,886,656 | 6/1975 | Meshulam et al. . |
| 4,014,622 | 3/1977 | Lotz . |
| 4,060,897 | 12/1977 | Greenstein ............................. 433/144 |
| 4,251,113 | 2/1981 | Mitin et al. . |
| 4,458,420 | 7/1984 | Davis ........................................ 30/342 |
| 4,777,725 | 10/1988 | Hirsch . |
| 4,976,684 | 12/1990 | Broadnax, Jr. .......................... 606/223 |
| 5,000,683 | 3/1991 | Brock . |
| 5,152,631 | 10/1992 | Bauer . |
| 5,743,880 | 4/1998 | Hlavaka .................................. 606/167 |

OTHER PUBLICATIONS

American Dental Supply, Inc. literature entitled "introducing . . . Flexi–Tips," published the week of Nov. 3, 1997.

*Primary Examiner*—Ralph A. Lewis
*Attorney, Agent, or Firm*—Fay, Sharpe, Beall, Fagan, Minnich & McKee LLP

[57] ABSTRACT

A flexible cutting tool includes a substantially cylindrically-shaped housing having a first end and a second end. The first end includes a hollowed region. A substantially cylindrically-shaped bushing, having a first face and second face and including a flexible material, is sized such that the first face and at least a portion of the bushing are secured inside the hollowed region of the housing. The bushing includes a bore extending through the first face, the second face, and an axis of the bushing. A cutting tool includes a cutting edge, a stop, and a shaft between the cutting edge and the stop. A diameter of the stop is larger than a diameter of the bore for allowing the stop to enter the second face of the bushing, frictionally pass through the bushing and exit the first face of the bushing. A diameter of the shaft is smaller than the diameter of the stop and larger than the diameter of the bore such that the bushing frictionally engages the shaft. A length of the shaft is longer than a thickness of the bushing. A flexibility of the cutting tool is a function of an amount of the shaft extending from the second face of the bushing.

20 Claims, 5 Drawing Sheets

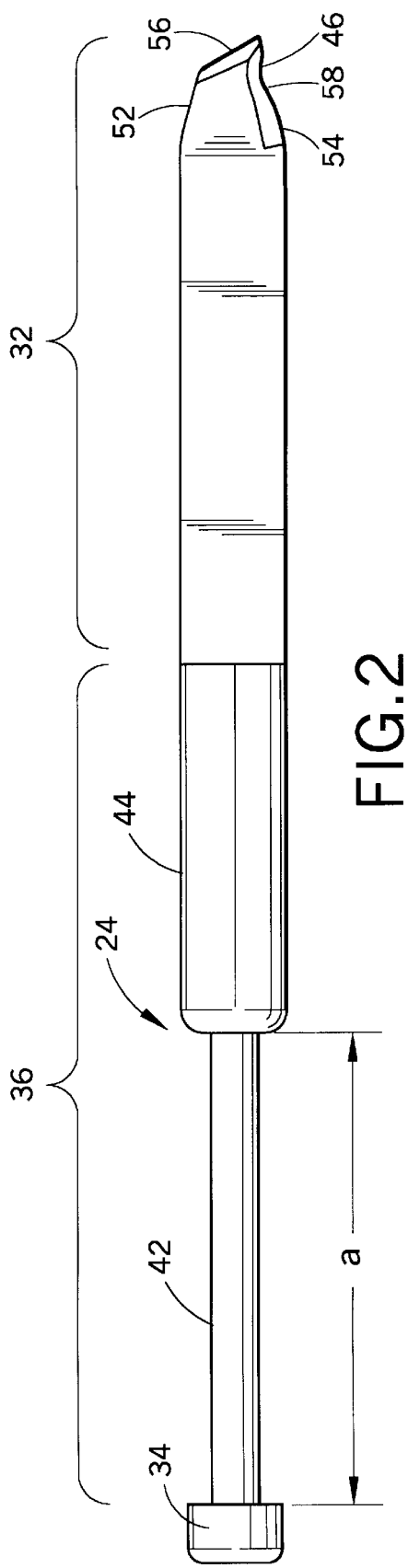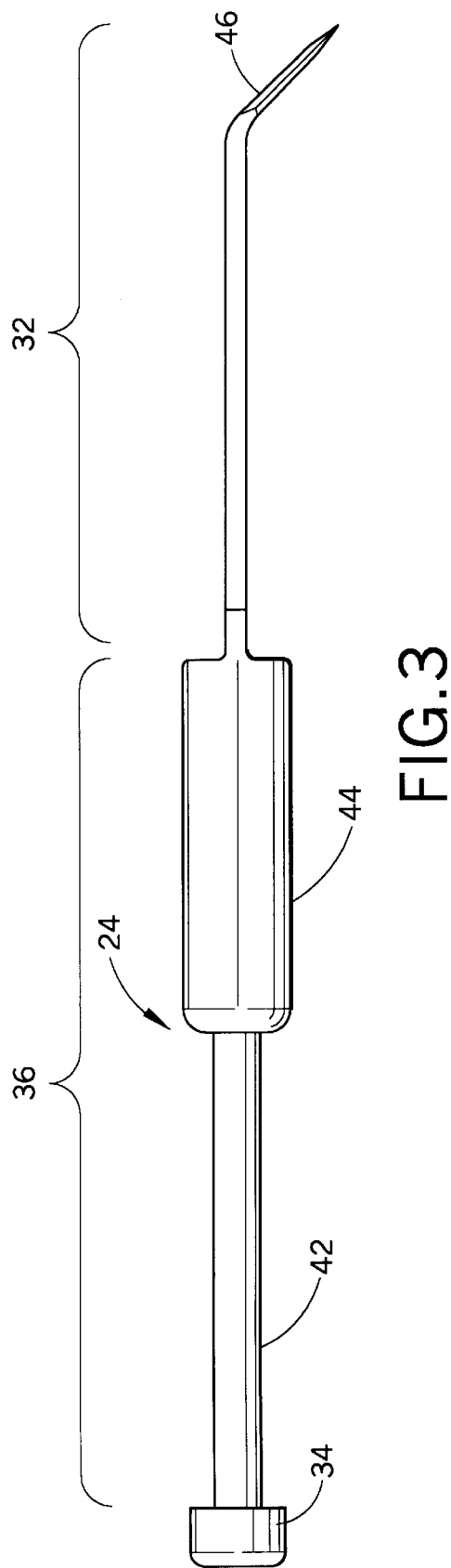

5,934,905

FLEXIBLE SCULPTING TOOL FOR DENTAL UNITS

This application claims the benefit of U.S. Provisional Patent Application Ser. No. 60/043,363 (filed Apr. 1, 1997).

BACKGROUND OF THE INVENTION

The present invention relates to the dental sculpting arts. It finds particular application in conjunction with hand held dental instruments for use in sculpting porcelain dental units, such as bridges, crowns, molars and premolars and will be described with particular reference thereto. It will be appreciated, however, that the invention will also find application in conjunction with sculpting other units.

Heretofore, dental technicians commonly use rigid, heavy tools for sculpting (e.g., carving) dental units. The rigidity of the carving edge (e.g., spatula) on these conventional carving tools makes it difficult for even experienced technicians to sculpt anatomically accurate dental units. Novices who are developing their sculpting skills are frustrated even more. Furthermore, heavy assemblies associated with the tools cause any user to become uncomfortable and tired after a short time, negatively affecting the quality of the product produced.

Traditional dental sculpting tools include a single, inflexible structure having a spatula at one end and a handle at the other end. In order to sculpt a material such as porcelain, a user holds the handle and carves the material with the spatula. The spatula is rigidly connected to the handle such that the handle transmits all movements and forces from the user's hand to the porcelain being sculpted. In other words, there is no flexibility built into the sculpting tool for absorbing and moderating unintended harsh movements from the user's hand. Therefore, harsh movements resulting from jerks or twitches in the user's hand produce unintended cuts in the material. These unintended cuts result in a structure which does not precisely and accurately represent the anatomy it is meant to depict.

A considerable amount of time is needed to develop the skills required for properly sculpting porcelain dental units. The conventional sculpting tools only tend to increase the amount of time necessary for acquiring those skills and frustrate students. In other words, conventional sculpting tools cannot be adjusted to accommodate different users' techniques. Instead, dental sculptors are currently forced to adjust their techniques to accommodate a narrow range of flexibility offered by conventional sculpting tools.

The present invention provides a new and improved apparatus and method which overcomes the above-referenced problems and others.

SUMMARY OF THE INVENTION

A sculpting instrument includes a housing having a first end and a second end. A hollowed region extends into the housing from the first end. A bushing has a first face and a second face. The first face of the bushing is secured at the first end of the housing. The bushing includes a flexible material and a bore extending through the first face, the second face, and an axis of the bushing. A cutting tool includes a cutting edge, a stop, and a shaft between the cutting edge and the stop. A diameter of the shaft is smaller than the diameter of the stop and larger than the diameter of the bore such that the bushing frictionally engages the shaft. A flexibility of the cutting tool is a function of an amount of the shaft extending from the second face of the bushing.

In accordance with one aspect of the invention, the hollowed region extends substantially to the second end of the housing.

In accordance with another aspect of the invention, the hollowed region is sized for securing at least the first face and a portion of the bushing secured at the first end of the housing.

In accordance with a more limited aspect of the invention, the housing further includes a second hollowed region having a diameter smaller than the first hollowed region. The second hollowed region is adjacent the first hollowed region and is sized for at least accepting the stop and the shaft when none of the shaft extends from the second face of the bushing.

One advantage of the present invention is that it is possible to adjust the flexibility of the cutting tool to accommodate the user's preferences. More specifically, the user can extend more of the shaft from the second face of the bushing to increase the flexibility of the cutting tool. Conversely, the user can extend less of the shaft from the second face of the bushing to decrease the flexibility of the cutting tool.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 2 illustrates a top view of a cutting tool of the invention;

FIG. 3 illustrates a side view of the cutting tool shown in FIG. 2;

DETAILED DESCRIPTION OF THE PREFERRED EMBODIMENTS

Figure 1:
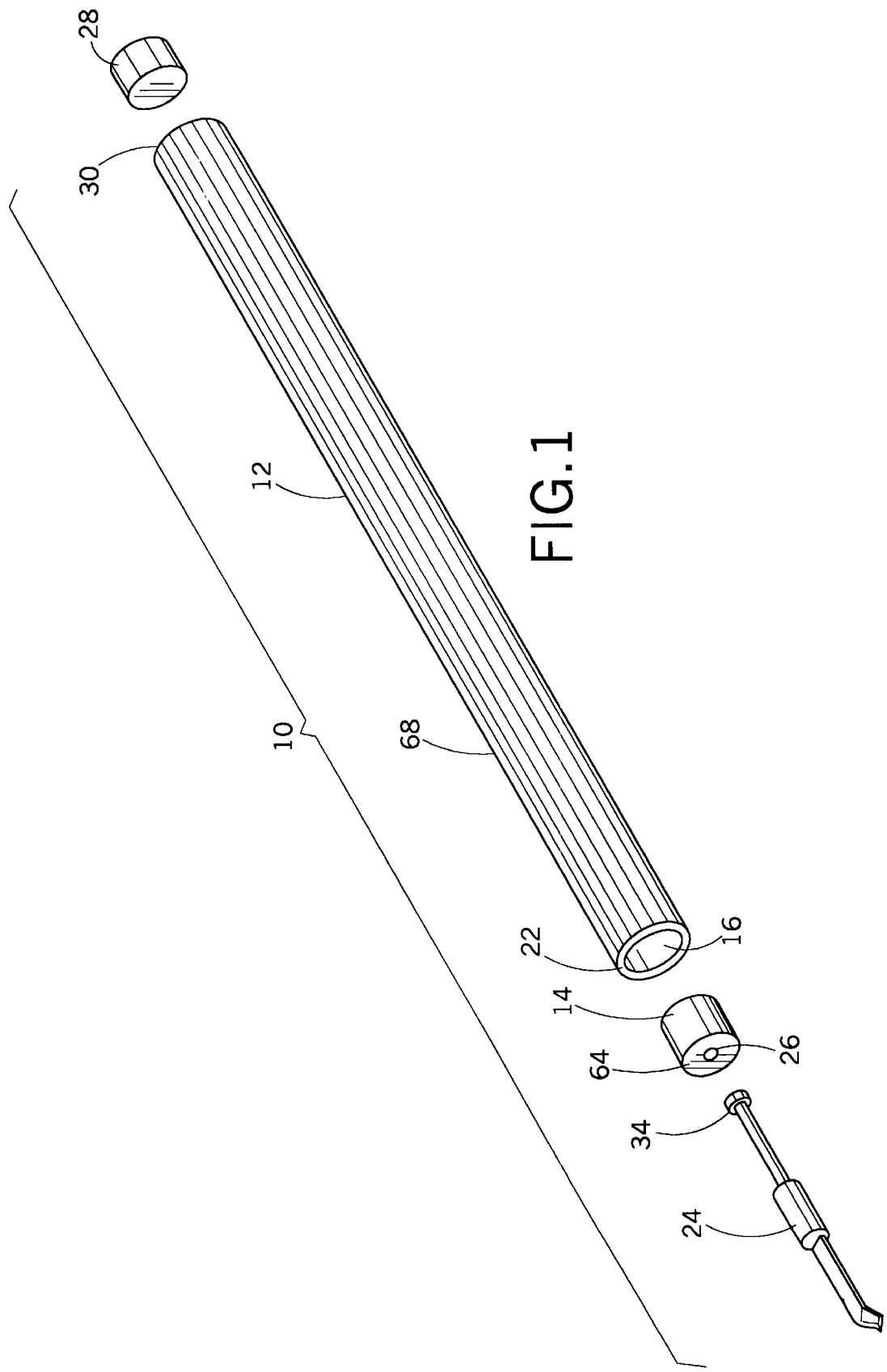
FIG. 1 illustrates an exploded view of the flexible sculpting tool according to the present invention.

With reference to FIG. 1, a flexible sculpting tool 10 includes a housing 12, a bushing 14 frictionally secured within a hollowed region 16 at a first end 22 of the housing 12, a cutting tool 24 frictionally secured within a bore 26 of the bushing 14 and an end cap 28 secured to a second end 30 of the housing 12.

FIG. 2 illustrates a top view of the cutting tool 24. The tool 24 includes a cutting portion 32, a stop 34, and a main body 36 between the cutting portion 32 and the stop 34. The main body 36 includes a shaft 42, having a length a, connected to the stop 34 and a connecting portion 44 joined to the cutting portion 32. The cutting portion 32 includes a blade 46 at a forward end.

In a preferred embodiment, the cutting tool 24 is approximately 1.5 inches long and includes a metal material (e.g., S30300 stainless steel). The stop 34 and connecting portion 44 are preferably 0.063 inches long and 0.401 inches long, respectively, and are substantially cylindrical with an outside diameter of approximately 0.094 inches. The shaft 42 is also preferably substantially cylindrical, has an outside diameter of approximately 0.047 inches, and is approximately 0.375inches long. The cutting portion 32 preferably is substantially flat and is approximately 0.661 inches long. The blade 46 preferably includes 6° front and rear cuts 52, 54, respectively, a side cut 56 of 45° and a notch 58. While the various cuts of the blade described in the preferred embodiment make the cutting tool 24 suitable for carving or sculpting porcelain, it is to be understood that blades including other configurations, suitable for sculpting porcelain and/or other materials, are also contemplated. Similarly, while a preferred embodiment including specific dimensions for the cutting tool 24 has been described, it is to be understood that other embodiments, having cutting tools with other dimensions, are also contemplated.

FIG. 3 illustrates a side view of the cutting tool 24 shown in FIG. 2. The substantially flat shape of the cutting portion 32 and the angle of the blade 46 are apparent from the tool 24 shown in FIG. 3.

With reference to FIGS. 1 and 4–6, the bushing 14 is substantially cylindrically-shaped. The bore 26 extends through a central axis of the bushing and has a slightly smaller diameter than the shaft 42. The bushing 14 includes a flexible material (e.g., rubber or flexible plastic). Although the stop 34 and the shaft 42 have larger diameters than the bore 26, the flexible material included in the bushing 14 allows the stop 34 and the shaft 42 to pass through the bore 26. More specifically, during assembly of the sculpting tool 10, a user aligns the stop 34 with a first end 60 of the bore 26. The user then applies sufficient force to push the stop 34 into the bore 26. Once the stop 34 is in the bore 26, the user continues to push the stop 34 through the length of the bore 26 until it exits the second end 62 of the bore 26. Once the stop 34 exits the second end 62 of the bore 26, the shaft 42 is frictionally secured within the bore 26 due to the slight difference in diameters. This process is reversed during disassembly.

Figure 4:
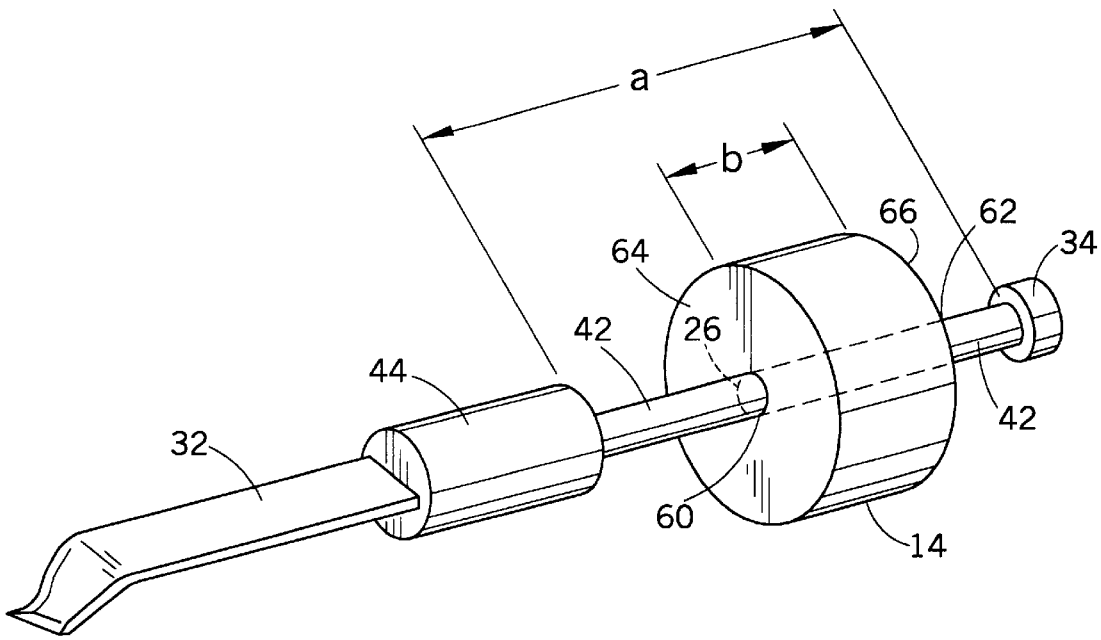
FIG. 4 illustrates an isometric view of a bushing of the invention.
Figure 5:
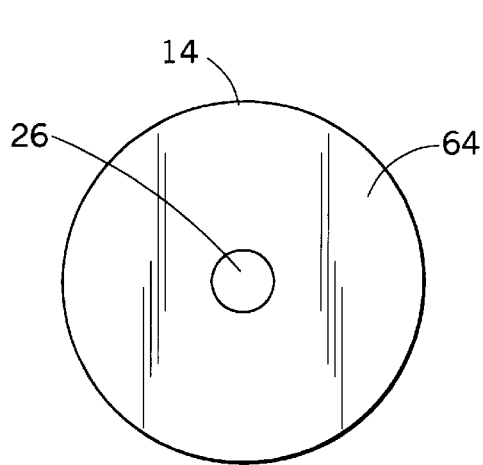
FIG. 5 illustrates a top view of the bushing.
Figure 6:
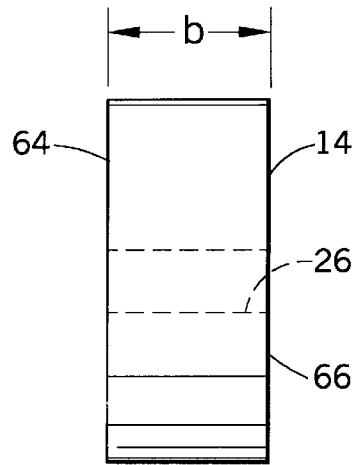
FIG. 6 illustrates a side view of the bushing shown in FIG. 5.

As illustrated in FIG. 4, the length a of the shaft 42 is preferably greater than a thickness b of the bushing 14. Therefore, the shaft 42 rides within the bushing 14. The connecting portion 44 and stop 34 at either end of the shaft 42, which have diameters larger than both the shaft 42 and the bore 26, contact the first and second faces 64, 66, respectively, of the bushing 14 for defining the range of movement of the cutting tool 24 within the bushing 14.

In the preferred embodiment, the flexible material of the bushing 14 is 45 shore "A" durometer rubber. However, it is to be understood that other flexible materials are also contemplated. Also, in the preferred embodiment described above, the bushing 14 has a diameter of approximately 0.25 inches and a thickness of approximately 0.188 inches. The diameter of the bore 26 in that embodiment is approximately 0.040 inches. While these dimensions describe the preferred embodiment, it is to be understood that other embodiments having other dimensions are also contemplated.

Figure 7:
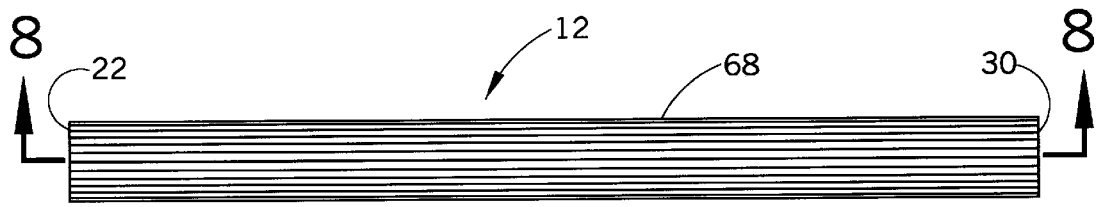
FIG. 7 illustrates a top view of a housing of the present invention.
Figure 8:
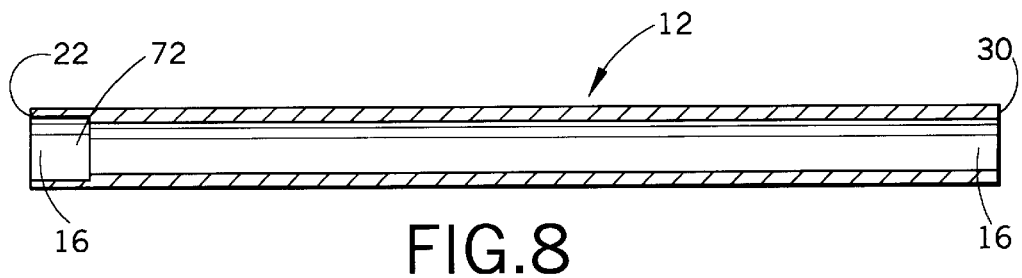
FIG. 8 illustrates a cross-sectional view of the housing of FIG. 7.

With reference to FIGS. 1, 7 and 8, the housing 12 is substantially cylindrical. In the preferred embodiment, the hollowed region 16 extends through the length of the housing 12, including the first and second ends 22, 30, respectively. A diameter of the hollowed region 16 at the first end 22 of the housing 12 is larger than a diameter at the second end 30, thereby defining a well 72 at the first end 22 of the housing 12. Preferably, the diameter of the well 72 is sized for frictionally securing the bushing 14 and the depth of the well 72 is sized such that, when the bushing 14 is fully seated within the well 72, the first face (i.e., exposed face) 64 of the bushing 14 is substantially flush with the first end 22 of the housing 12. When the bushing 14 is secured within the well 72, and the cutting tool 24 is positioned such that the connecting portion 44 contacts the exposed face 64 of the bushing 14, the stop 34 and a portion of the shaft 42 protrude into the hollowed region 16. Preferably, the outer surface 68 of the housing 12 is beveled and/or rounded at the first end 22 and the second end 30 to avoid snagging and/or personal injury to a user. Also, the housing 12 preferably includes a metal material (e.g., 6061-T6 aluminum round tubing). However, it is to be understood that it is also contemplated that the housing includes other materials (e.g., a plastic).

In the preferred embodiment, the outside diameter of the housing is 0.3125 inches and the housing is 5.00 inches long. Furthermore, the well 72 preferably has a diameter of 0.234 inches and a depth of 0.188 inches. Therefore, the bushing 14 in the preferred embodiment, which has a diameter of 0.25 inches, is frictionally secured inside the well 72. Optionally, a glue or other adhesive may be used to permanently secure the bushing 14 within the well 72. While these dimensions describe the preferred embodiment of the housing, it is to be understood that other embodiments of the housing having other dimensions are also contemplated.

Figure 9:
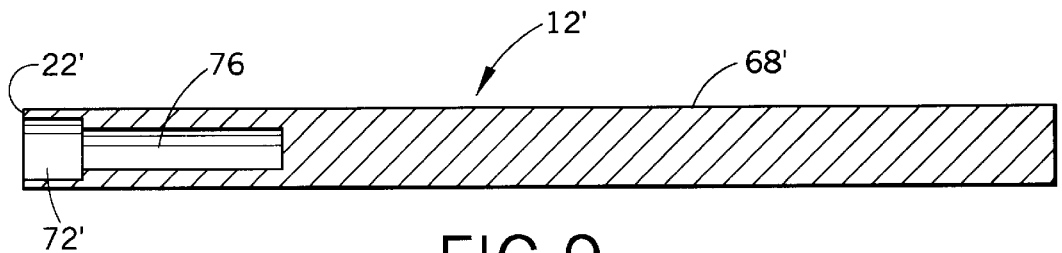
FIG. 9 illustrates a cross-sectional view of an alternate embodiment of the housing.

FIG. 9 illustrates an alternate embodiment of the housing. For ease of understanding this embodiment, like components are designated by like numerals with a primed (') suffix and new components are designated by new numerals. In this embodiment of the housing 12', the hollowed region 16' does not extend through the length of the housing 12'. Instead, the hollowed region 16' only consists of the well 72' and a second well 76 adjacent to the first well 72'. The diameter of the second well 76 is smaller than the diameter of the first well 72', but is sized for accepting the stop and shaft of the cutting tool. Ideally, the second well 76 is positioned such that the depth of the first well 72' allows the first end (exposed end) of the bushing to be substantially flush with the first end 22' of the housing 12' when the bushing is seated in the well. However, embodiments in which the exposed face of the bushing is not substantially flush with the first end 22' of the housing 12' are also contemplated. As in the preferred embodiment, the first well 72' is sized for frictionally securing the bushing.

In this embodiment, the outside diameter of the housing 12' is 0.3125 inches and the housing 12' is 5.00 inches long. Furthermore, the well 72' has a diameter of 0.234 inches and a depth of 0.188 inches. Therefore, a bushing having a diameter of 0.25 inches is frictionally secured inside the well 72'. The second well 76 has a diameter of 0.215 inches and is 0.625 inches deep. While these dimensions describe this alternate embodiment of the housing, it is to be understood that other embodiments of the housing having other dimensions are also contemplated.

Figure 10:
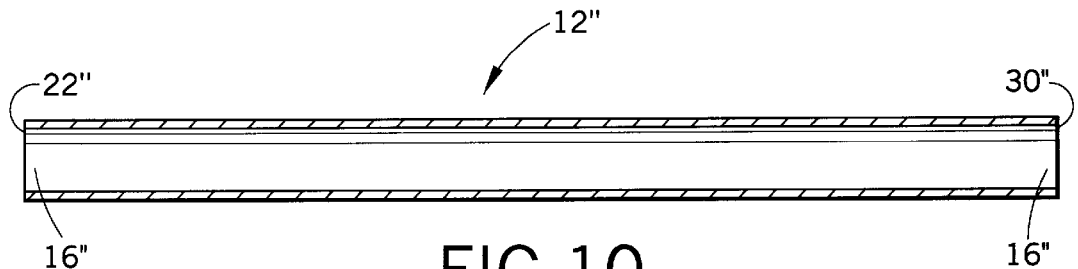
FIG. 10 illustrates a cross-sectional view of another alternate embodiment of the housing.

FIG. 10 illustrates another alternate embodiment of the housing. For ease of understanding this embodiment, like components are designated by like numerals with a double-primed (") suffix and new components are designated by new numerals. In this embodiment of the housing 12", the hollowed region 16" is substantially a uniform diameter and extends the entire length of the housing 12". It is contemplated that the bushing is secured within the hollowed region 16" by friction and/or an adhesive. Alternatively, it is also contemplated that the bushing have a larger diameter than the hollowed region 16" so that it is simply secured to the end 22" of the housing 12" using an adhesive.

Figure 11:
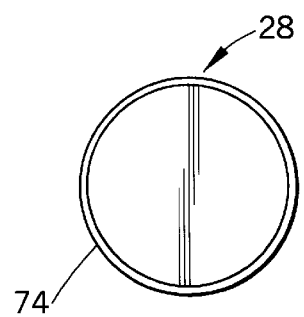
FIG. 11 illustrates a top view of a cap of the invention.
Figure 12:
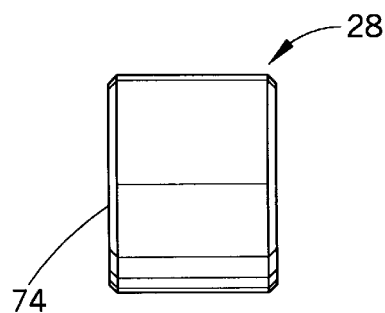
FIG. 12 illustrates a side view of the cap shown in FIG. 10.

With reference to FIGS. 1, 11 and 12, the cap 28 of the preferred embodiment is substantially cylindrically-shaped and sized to fit at the second end 30 of the housing 12. Preferably, the cap 28 is secured to the second end 30 of the housing 12 using a glue or other adhesive. However, other materials and means for securing the cap 28 to the end 30 of the housing 12 are also contemplated. Preferably, the outer edges 74 of the cap 28 are beveled or rounded to avoid snagging and/or personal injury to a user. Also, in the preferred embodiment, the cap 28 includes a metal material (e.g., 6061-T6 aluminum), has an outside diameter of 0.250 inches, and is 0.188 inches long. While this material and these dimensions describe the preferred embodiment of the cap, it is to be understood that other embodiments of the cap including other materials and/or dimensions are also contemplated.

Figure 13:
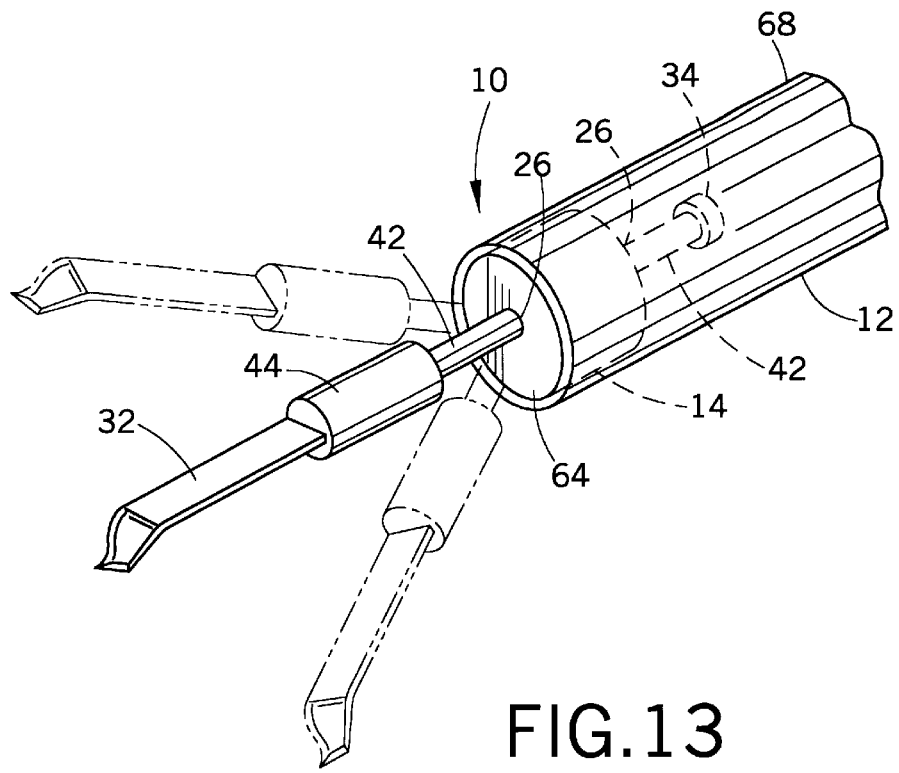
FIG. 13 illustrates the sculpting tool having a great range of flexibility.
Figure 14:
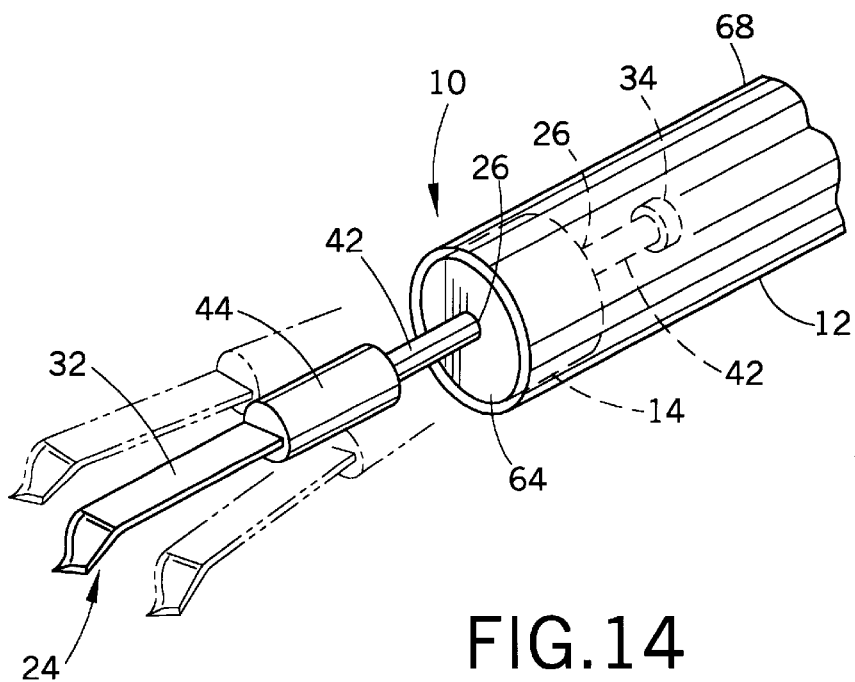
FIG. 14 illustrates the sculpting tool having a limited range of flexibility.

With reference to FIGS. 13 and 14, a length of the shaft 42 extending from the bore 26 of the bushing 14 is set by the user to adjust the flexibility of the cutting tool 24. Dashed lines in FIGS. 13 and 14 indicate the flexibility of the tool 24. More specifically, a user increases the length of the shaft 42 extending from the exposed face 64 of the bushing 14 when more flexibility is desired, as illustrated in FIG. 13. Conversely, a user decreases the length of the shaft 42 extending from the exposed face 64 of the bushing 14 when less flexibility is desired, as illustrated in FIG. 14. In this manner, the user is able to use his judgment to adjust the flexibility of the cutting tool 24 to accommodate the conditions of the material being sculpted.

For example, when the material being sculpted is wet, it is typically soft. Under these conditions, it is preferable to make soft cuts. To achieve this, more flexibility of the cutting tool 24 is desirable. Therefore, the user pulls the cutting tool 24 and extends it from the bushing 14. When the material being sculpted is dry, it is typically more rigid. Therefore, it is preferable to make hard (e.g., rigid) cuts. To achieve this, less flexibility on the cutting tool 24 is desirable. Therefore, the user pushes the cutting tool 24 into the bushing 14 until the desired amount of resistance from the bushing 14 is attained. In this manner, the user determines a final position of the cutting tool 24 based on the conditions of the material being sculpted. Similarly, the user adjusts the position of the cutting tool 24 within the bushing 14 based upon personal preference. Therefore, the flexible sculpting tool 10 satisfies the most demanding user.

While specific dimensions and angles associated with the flexible dental tool disclosed in the present invention have been discussed, it is to be understood that other dimensions and angles are also contemplated. Similarly, while preferred materials have been disclosed for constructing the flexible dental tool, it is to be understood that other materials are also contemplated.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A sculpting instrument, comprising:
    a housing having a first end and a second end and a hollowed region extending into the housing from the first end;
    a bushing having a first face and a second face, the first face of the bushing being secured at the first end of the housing, the bushing including a flexible material and a bore extending through the first face, the second face, and an axis of the bushing; and
    a cutting tool including a cutting edge, a stop, and a shaft between the cutting edge and the stop, a diameter of the shaft being smaller than the diameter of the stop and larger than the diameter of the bore such that the bushing frictionally engages the shaft, a flexibility of the cutting tool being a function of an amount of the shaft extending from the second face of the bushing.

2. The sculpting instrument according to claim 1, wherein the cutting edge includes a blade.

3. The sculpting instrument according to claim 2, wherein the blade is angled at about 45°.

4. The sculpting instrument according to claim 1, wherein the bushing includes a rubber material.

5. The sculpting instrument according to claim 1, wherein the hollowed region extends substantially to the second end of the housing.

6. The sculpting instrument according to claim 5, further including:
    a cap for sealing the second end of the housing.

7. The sculpting instrument according to claim 1, wherein the hollowed region is sized for securing at least the first face and a portion of the bushing secured at the first end of the housing.

8. The sculpting instrument according to claim 7, wherein the housing further includes:
    a second hollowed region having a diameter smaller than the first hollowed region, the second hollowed region being adjacent the first hollowed region and being sized for at least accepting the stop and the shaft when none of the shaft extends from the second face of the bushing.

9. The sculpting instrument according to claim 1,
    wherein the flexibility of the cutting tool increases as more of the shaft extends from the second face of the bushing; and
    wherein the flexibility of the cutting tool decreases as less of the shaft extends from the second face of the bushing.

10. The sculpting instrument according to claim 1, wherein a length of the shaft is longer than a thickness of the bushing.

11. A cutting tool, comprising:
    a substantially cylindrically-shaped housing having a first end and a second end, the first end including a hollowed region;
    a substantially cylindrically-shaped bushing having a first face and second face and including a flexible material, the bushing being sized such that the first face and at least a portion of the bushing are secured inside the hollowed region of the housing, the bushing including a bore extending through the first face, the second face, and an axis of the bushing; and a cutting tool including a cutting edge, a stop, and a shaft between the cutting edge and the stop, a diameter of the stop being larger than a diameter of the bore for allowing the stop to enter the second face of the bushing, frictionally pass through the bushing and exit the first face of the bushing, a diameter of the shaft being smaller than the diameter of the stop and larger than the diameter of the bore such that the bushing frictionally engages the shaft, a length of the shaft being longer than a thickness of the bushing, and a flexibility of the cutting tool being a function of an amount of the shaft extending from the second face of the bushing.

12. The cutting tool according to claim 11, wherein the cutting edge includes a blade which is angled.

13. The cutting tool according to claim 11, wherein the housing includes a metal material.

14. The cutting tool according to claim 11, wherein the hollowed region extends substantially from the first end of the housing to the second end of the housing.

15. The cutting tool according to claim 11, further including:

a cap for sealing the second end of the housing.

16. The cutting tool according to claim 11, wherein the hollowed region extends a distance substantially equal to the thickness of the bushing whereby the second face of the bushing is substantially flush with the first end of the housing when the bushing is secured inside the hollowed region.

17. The cutting tool according to claim 16, wherein the housing further includes:

a second hollowed region having a diameter smaller than the first hollowed region, the second hollowed region being adjacent the first hollowed region and having a depth at least for accepting the stop and the shaft when none of the shaft extends from the second face of the bushing.

18. The cutting tool according to claim 11, wherein the flexibility of the cutting tool increases as more of the shaft extends from the second face of the bushing; and wherein the flexibility of the cutting tool decreases as less of the shaft extends from the second face of the bushing.

19. A method of sculpting a dental unit using a flexible cutting tool, the method including:

adjusting a flexibility of a cutting edge located at one end of the flexible cutting tool;

grasping a handle located at a second end of the flexible cutting tool;

applying a cutting edge of the cutting tool to the dental unit;

sculpting the dental unit, harsh movements transmitted from a user to the handle being moderated by the flexibility of the cutting tool whereby a full force of the harsh movement is not transmitted to the dental unit.

20. The method of sculpting a dental unit according to claim 19, wherein the cutting tool includes the cutting edge at a first end, a stop at a second end, and a shaft between the cutting edge and the stop, and wherein the flexible cutting tool includes a bushing, frictionally secured within the first end of the flexible cutting tool, having a bore extending through the bushing, a diameter of the stop being larger than a diameter of the bore, a diameter of the shaft being smaller than the diameter of the stop and larger than the diameter of the bore such that the bushing frictionally engages the shaft, the adjusting step including at least one of:

increasing an amount of the shaft extending from an external face of the bushing for increasing the flexibility of the cutting edge; and decreasing an amount of the shaft extending from the external face of the bushing for decreasing the flexibility of the cutting edge.

* * * * *